United States Patent [19]

David

[11] Patent Number: 5,188,323
[45] Date of Patent: Feb. 23, 1993

[54] AMBULATORY SUPPORT APPARATUS

[75] Inventor: Henry B. David, Glendale, Calif.

[73] Assignee: Melco Wire Products Co., San Fernando, Calif.

[21] Appl. No.: 833,380

[22] Filed: Feb. 10, 1992

[51] Int. Cl.⁵ .............................................. F16M 13/00
[52] U.S. Cl. .................................. 248/158; 248/125; 248/297.2; 74/110
[58] Field of Search .................. 211/94, 162; 248/125, 248/218.4, 219.1, 219.2, 219.3, 219.4, 332, 338, 327, 328, 158, 320, 321, 297.2, 440.1, 161, 404; 254/385, 399; 74/89.22, 110; 474/101, 140

[56] References Cited

U.S. PATENT DOCUMENTS

| | | | |
|---|---|---|---|
| 262,661 | 8/1882 | Gordon | 248/297.2 X |
| 624,848 | 5/1899 | McCousland | 248/158 |
| 1,636,771 | 7/1927 | Glaberman | 248/158 |
| 1,740,520 | 12/1929 | Murphy | 248/335 |
| 2,591,685 | 4/1952 | Du Mais et al. | 248/125 |
| 2,631,582 | 3/1953 | Bensfield | 254/385 X |
| 2,670,168 | 2/1954 | Magnan et al. | 248/297.2 |
| 2,696,963 | 12/1954 | Shepherd | 248/161 |
| 2,814,457 | 11/1957 | Phelan | 248/328 |
| 3,191,903 | 6/1965 | Weiland | 248/328 |
| 3,462,110 | 8/1969 | Chelslock | 248/219.4 |
| 3,642,241 | 2/1972 | Kaufman | 248/327 |
| 3,805,054 | 4/1974 | Wolf | 248/320 X |
| 4,005,851 | 2/1977 | Plote | 254/385 |
| 4,469,031 | 9/1984 | Haycock | 248/218.4 X |
| 4,673,154 | 6/1987 | Karapita | 268/320 |
| 4,725,027 | 2/1988 | Bekanich | 248/311.3 X |
| 4,865,283 | 9/1989 | Parker | 211/162 X |
| 5,086,930 | 2/1992 | Saeks | 248/161 X |
| 5,110,076 | 5/1992 | Snyder | 248/125 |

Primary Examiner—Carl D. Friedman
Assistant Examiner—Korie H. Chan
Attorney, Agent, or Firm—Michael A. Painter

[57] ABSTRACT

An apparatus for supporting medical supplies which is ambulatory and provides improved load-support capabilities. A vertical standard is mounted upon an ambulatory base and includes a plurality of independent fluid or equipment hanger assemblies. Each hanger assembly is vertically movable and is capable of supporting substantial loads (e.g., 25 pounds). A pulley system is coupled to the hanger assembly and an engagement positioner. The pulley system transmits the selected vertical movement of the engagement positioner to the hanger assembly while concurrently reducing the mechanical force required to position the load suspended from the respective hanger assembly.

6 Claims, 3 Drawing Sheets

AMBULATORY SUPPORT APPARATUS

BACKGROUND OF THE INVENTION

1. Field of the Invention

The present invention is generally related to utility support structures, and more particular to ambulatory apparatus adapted to support medical supplies or equipment.

2. Prior Art

The purpose of the present invention is to provide an improved apparatus which can support pumps, tubes, hoses, containers of fluid or other accessories specifically for use in medical applications. To be used for the defined applications, the equipment must be ambulatory and thereby be easily moved from location to location. Because of the environment in which the present invention is intended to be used, it must exhibit a high degree of stability. Loads which must be supported by the apparatus can be heavy and therefore difficult to handle. In addition, where the load comprises a fluid which is being dispensed to a patient, pressure requirements dictate the load be vertically moveable to the selected height.

The classical device taught by the prior art is typically defined by a vertical pole supported by three or four equally spaced legs coupled at the lower terminus of the pole. Even if the supporting legs are provided with ambulatory casters, the device is susceptible of overturning since support is provided only at minimum intervals of 90° of arc. To support a load, a vertical standard is provided with fixed vertical couplings from which medical equipment or fluids are suspended. The problems inherent in this type of device are evident. Under the conditions which typically exist in operating theaters or otherwise, the availability of large volumes of fluid are often required. The devices taught by the prior art require medical personnel to manually lift or otherwise change the position of the fluid reservoirs, a task which can be difficult and often dangerous under the conditions of use.

Another device taught by the prior art provides for the mechanical adjustment of a plurality of hanger supports, each of which is adapted to position a container of fluid. Each hanger support is directly coupled to a locking assembly or positioner, the movement of which is directly reflected in the repositioning of the hanger support. Although this device provides for the mechanical repositioning of a supported load, it provides no mechanical advantage to the user thereby making it extremely burdensome for use in applications requiring the support of heavy loads.

The present invention substantially resolves those problems exhibited by the devices disclosed in the prior art. A stable, ambulatory vertical standard comprises a plurality of adjacent tracks, each track being adapted to support an independent fluid hanger. Each fluid hanger is coupled to a pulley assembly disposed within a positioning track. The pulley assembly provides a mechanical advantage of at least 2:1 while simultaneously reversing the direction of force which must be used to move the fluid hanger upwardly or downwardly. Upward or downward movement of each fluid hanger is determined by the selected arrangement of a positioning arm. The positioning arm is coupled to the pulley assembly, the direction of movement of the respective fluid hanger being inversely related to the direction of the movement of the positioning arm. This allows the user to effectively employ his or her weight to impose upward movement to a fluid container which is suspended from a fluid hanger.

To enhance the stability of the present invention, the vertical standard is coupled to an inverted base. The base comprises a hub and a complement of at least five uniformly spaced supporting legs radiating outwardly from the hub and lower terminus of the vertical standard. The end of each leg opposite the hub is coupled to a conventional caster. Stability is provided by vertically disposing the interface between the standard and the hub at a level which is lower than the interface between the supporting legs and the casters. The inverted interface at the hub lowers the center of gravity of the assembled apparatus.

SUMMARY OF THE INVENTION

The present invention comprises a utility supporting apparatus intended for medical applications. Although it is understood the present invention can be employed for supporting medical equipment and the like, the construction and use of the apparatus will be described with respect to the support of fluid containers. The typical environment in which the present invention will be used is an operating theater. Under such conditions, there are extensive requirements necessitating the availability of large volumes of fluid which are to be used either during a surgical procedure or while maintaining the condition of a patient. Where large fluid containers are employed, the weight thereof will be increased accordingly. It is an object of the present invention to independently support a plurality of large fluid containers, each weighing more than 25 pounds.

A central vertical standard is mounted upon an inverted base. The vertical standard comprises a plurality of independent extruded tracks, each of which define the vertical movement of an independent fluid hanger. A pulley assembly is disposed within an extruded track and coupled to a fluid hanger and a respective positioning arm. The pulley assembly provides a mechanical advantage of at least 2:1 and creates an inverse relationship between the direction of the force applied to the positioning arm and the movement of the fluid hanger. For stability, the vertical standard is mounted upon an inverted base which lowers the center of gravity of the supporting apparatus.

It is therefore an object of the present invention to provide an improved utility supporting apparatus.

It is another object of the present invention to provide an improved supporting apparatus incorporating a plurality of fluid hangers, each of which are independently moveable.

It is another object of the present invention to provide an improved supporting apparatus which allows a fluid container to be urged upwardly through the application of a downwardly directed force.

It is still yet another object of the present invention to provide an improved supporting apparatus which is simple and inexpensive to fabricate.

The novel features which are believed to be characteristic of the invention, both as to its organization and method of operation, together with further objectives and advantages thereof, will be better understood from the following description considered in connection with the accompanying drawing in which a presently preferred embodiment of the invention is illustrated by way of example. It is to be expressly understood, however,

DESCRIPTION OF THE PRESENTLY PREFERRED EMBODIMENT

Figure 1:
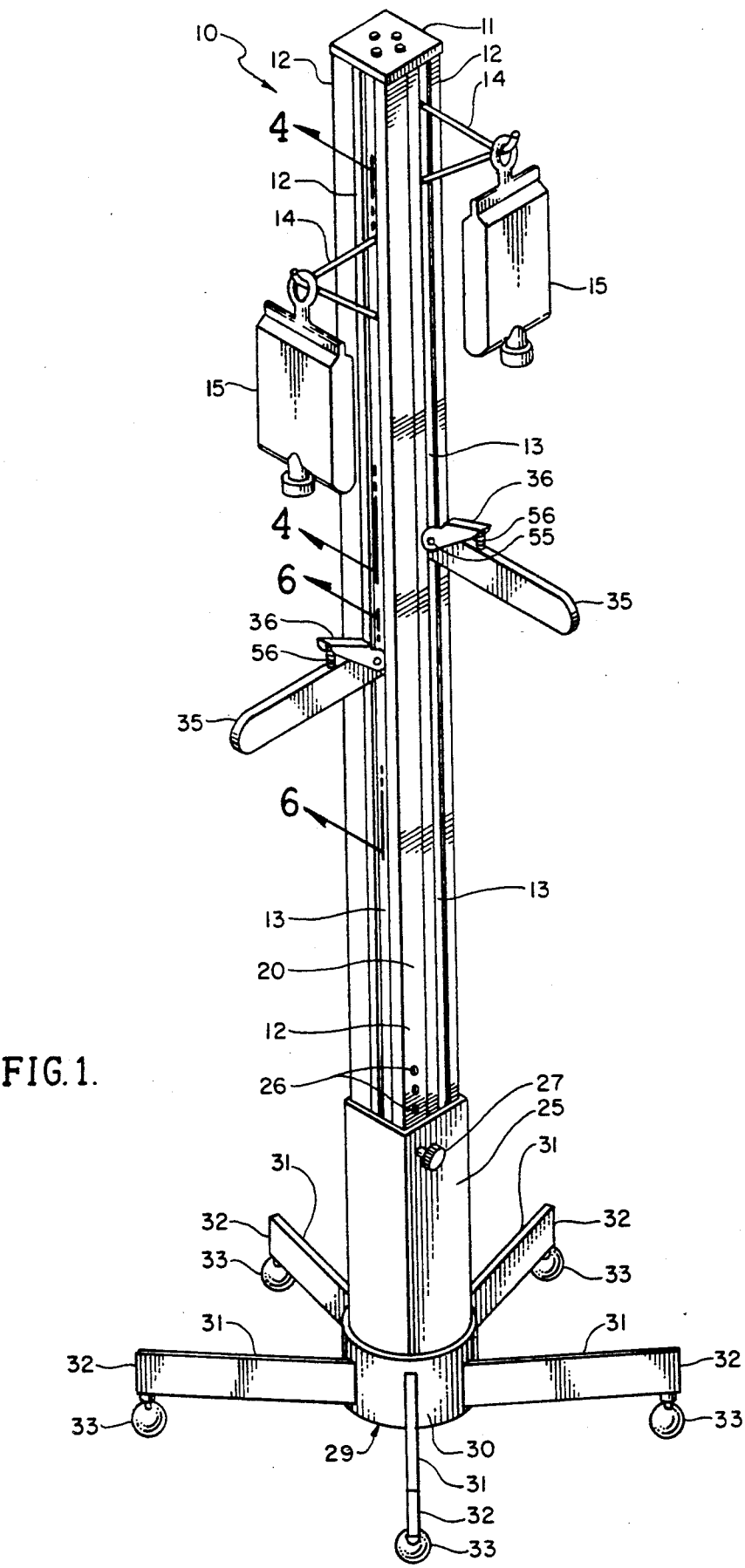
FIG. 1 is a perspective view of the present invention ambulatory supporting apparatus.
Figure 2:
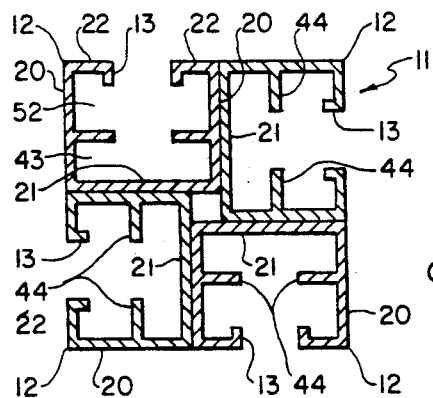
FIG. 2 is a top plan, cross-sectional view of the vertical standard shown in FIG. 1 taken through line 2—2 of FIG. 1.

An understanding of the present invention and the use thereof can be best gained by reference to FIG. 1 wherein a perspective view of the present invention is shown generally designated by the reference numeral 10. A vertical standard 11 consists of four extruded aluminum tracks 12 placed adjacent one another in parallel spaced relation to each other. As can be seen in FIG. 1 and FIG. 2, each extruded track 12 defines a uniform longitudinal aperture 13. In the preferred embodiment of the present invention 10 shown in FIG. 1 and FIG. 2, vertical standard 11 comprises four accessible lateral faces, each being separated by 90° of arc from adjacent faces. Each face exhibits the longitudinal aperture 13 along the full vertical length thereof.

As will be explained in detail hereinbelow, a fluid hanger 14 is adapted to be slidably engaged within and moveable along each of the longitudinal apertures 13. Although FIG. 1 illustrates only two fluid hangers 14, it is understood the scope of the present invention includes the use of up to four independently moveable fluid hangers 14. As an example of use, two fluid containers 15 are shown suspended from fluid hangers 14.

The assembly of vertical standard 11 can be best seen by reference to FIG. 2. In the preferred embodiment of the present invention, vertical standard 11 is fabricated from four extruded aluminum tracks 12 which are placed adjacent one another along longitudinal walls thereof. Each track 12 comprises a pair of side walls 20, rear wall 21 and a pair of front flanges 22 depending inwardly from the edges of side walls 20. The front flanges 22 define the uniform aperture 13 which extends the full length of each extruded track 12 (see FIG. 1). Extruded tracks 12 are placed adjacent one another whereby the aperture 13 is directed outwardly along each of the exposed faces of standard 11. In this configuration, each longitudinal aperture 13 is separated from an adjacent aperture 13 by 90° of arc.

When the present invention is employed to support fluid containers 15, the flow pressure of the fluid being dispersed is proportional to the vertical height of the fluid container relative to the fluid outlet. In addition to providing the capability to independently alter the vertical position of fluid hangers 14, the height of vertical standard 11 can itself be adjusted. As can be seen in FIG. 1, vertical standard 11 is slidably disposed within a coaxial receiving standard 25. In the preferred embodiment of the present invention, a plurality of circular apertures 26 are disposed in a side wall 20 of an extruded track 12. A positioning shaft 27 is resiliently coupled to receiving standard 25 and is adapted to be engaged within one of the circular apertures 26. Vertical standard 11 may be disposed at a selected height by engaging shaft 27 with a predetermined one of the circular apertures 26.

One of the objectives of the present invention is to provide a supporting apparatus having enhanced stability. To meet this objective, vertical standard 11 and receiving standard 25 are mounted upon an inverted base 29. Inverted base 29 is constructed of a hub 30 from which at least five supporting legs 31 extend radially outwardly therefrom. All supporting legs 31 are uniformly spaced from adjacent supporting legs 31. When using five supporting legs 31, each is spaced from an adjacent leg by 72° of arc. The objective of the present invention is principally met by lowering the center of gravity of vertical standard 11. At the terminus 32 of each supporting leg 31 opposite hub 30, supporting leg 31 is coupled to a conventional caster 33. To lower the center of gravity of vertical standard 11, each supporting leg 31 extends outwardly and upwardly from the interface between hub 30 and supporting leg 31. In this configuration, each leg will impose a horizontal force vector which will tend to counteract rotational forces which could otherwise cause the present invention to overturn.

The primary objective of the present invention supporting apparatus 10 is to reduce the effort required to position heavy fluid containers. As can be seen in FIGURE 1, fluid containers 15 are suspended from fluid hangers 14. Each fluid hanger 14 has associated therewith a positioning arm 35. Positioning arm 35 is slidably disposed within an extruded track 12 and extends from longitudinal aperture 13. The location of a positioning arm 35 along a longitudinal aperture 13 is determined by the release and/or engagement of positioning lever 36.

Figure 5:
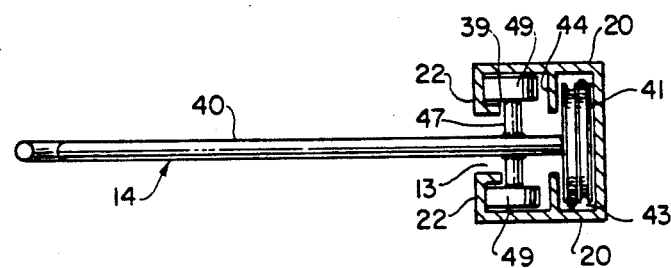
FIG. 5 is a cross-sectional view of the mounted fluid hanger shown in FIG. 4 taken through line 5—5 of FIG. 4.
Figure 4:
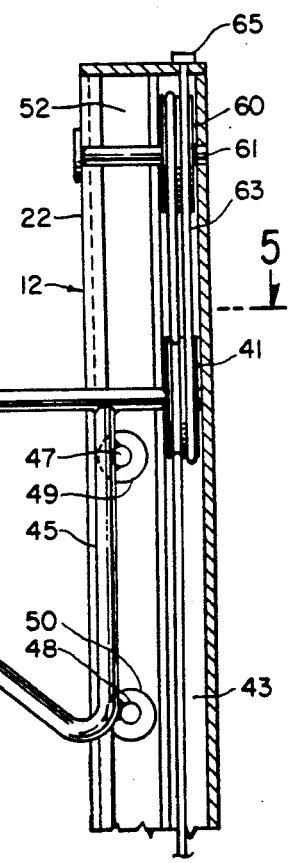
FIG. 4 is a side elevation, cross-sectional view of the interface between a fluid hanger and the vertical standard taken through line 4—4 of FIG. 1.

The construction of the fluid hangers 14 can be best seen by reference to FIGS. 4 and 5. Fluid hanger 14 comprises a horizontal supporting rod 40 which is disposed through the longitudinal aperture 13 formed by frontal flanges 22. A first pulley 41 is suitably journeled about the end 42 of supporting rod 40. As can be seen in FIG. 2, each extruded track 12 defines two substantially rectangular cavities 43 and 52 which are formed by segments of side walls 20, rear wall 21, interior flanges 44 and frontal flanges 22. A lateral entry to cavity 43 lies between interior flanges 44 and is aligned with longitudinal aperture 13. The width of cavity 43 (i.e., the distance between side walls 20) is greater than the diameter of first pulley 41. Cavity 43 is adapted to receive first pulley 41 which is freely rotatable about rod 40 within cavity 43.

To support the weight of a fluid container 15, fluid hanger 14 is constructed substantially in the form of a right triangle. To implement this configuration, horizontal supporting rod 40 is welded or otherwise connected to vertical member 45. Bracing member 46 forms the hypotenuse of the right triangle and is secured between the supporting end 53 of fluid hanger 14 and vertical member 45.

To provide for unobstructed movement of fluid hanger 14, upper and lower shafts 47 and 48 respectively, are secured to vertical member 45 and are perpendicular thereto. A pair of rollers 49 are suitably journeled at the ends of upper shaft 47 and are adapted to rollingly engage the surfaces of frontal flanges 22 of extruded track 12. Similarly, a pair of rollers 50 are suitable journeled at the ends of lower shaft 48. As can be best seen in FIG. 4 and FIG. 5, rollers 49 and 50 are disposed within cavity 52 and are adapted to rollingly engage the surfaces of frontal flanges 22 and interior flanges 44.

Figure 6:
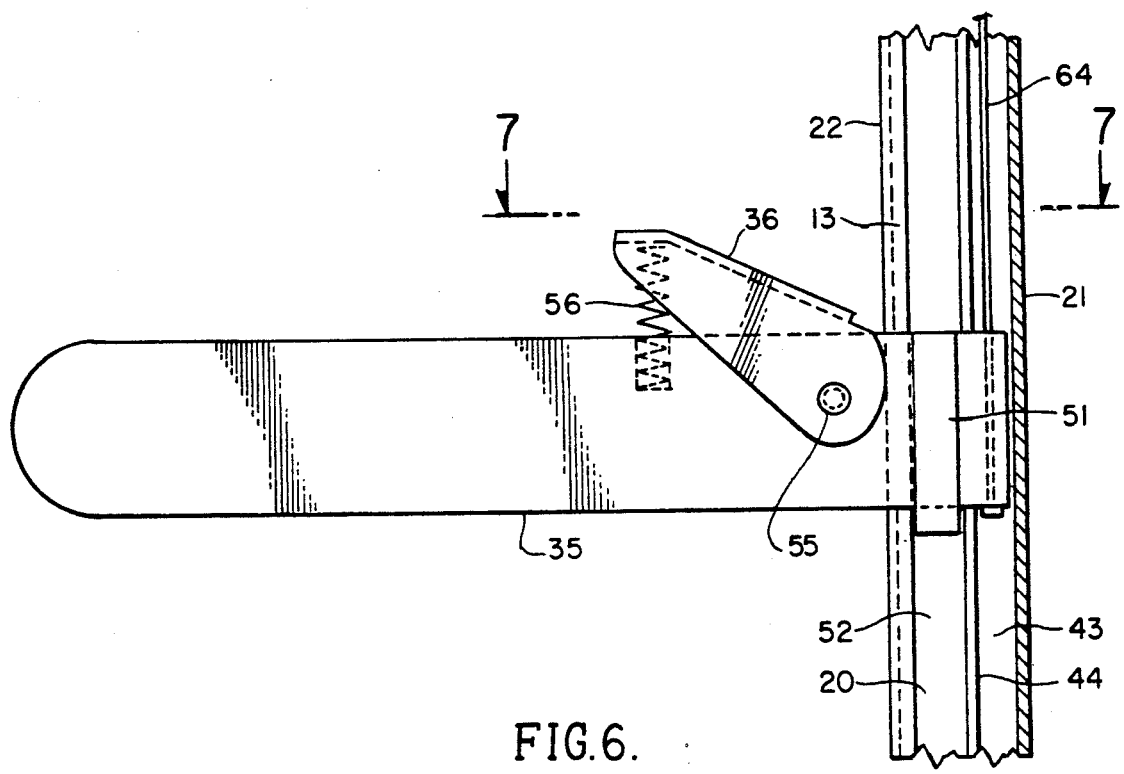
FIG. 6 is a side elevation, cross-sectional view of the interface between the engagement arm and the vertical standard shown in FIG. 1 taken through line 6—6 of FIG. 1.
Figure 7:
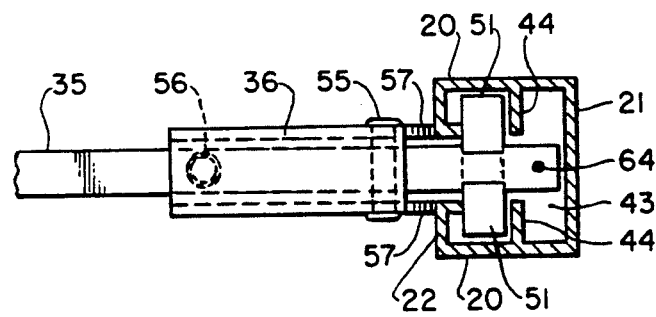
FIG. 7 is a cross-sectional view of the mounted engagement arm shown in FIG. 6 taken through line 7—7 of FIG. 6.

The structure of positioning arm 35 and positioning lever 36 can be best seen by reference to FIG. 6 and FIG. 7. Positioning arm 35 comprises a planar member which is adapted to be inserted within longitudinal aperture 13 and extend into cavity 43 of extruded track 12. To maintain the orientation of positioning arm 35, a pair of bracing flanges 51 extend outwardly from positioning arm 35 toward side walls 20 within cavity 52 defined by frontal flanges 22 and interior flanges 44. Engagement of positioning arm 35 at a selected location along extruded track 12 is accomplished through the engagement between positioning lever 36 and the surface of frontal flanges 22. Engagement lever 36 is pivotally coupled to positioning arm 35 about shaft 55. To provide for a resilient engagement force, helical spring 56 is coupled between positioning arm 35 and positioning lever 36. In its extended position, helical spring 56 will impose a force on positioning lever 36 causing it to rotate clockwise about shaft 55. The clockwise rotation of positioning lever 36 will result in frictional engagement between the engagement surfaces 57 of positioning lever 36 and the respective surfaces of frontal flanges 22. The imposition of a counterclockwise force on positioning lever 36 will compress helical spring 56 thereby removing the frictional engagement between positioning lever 36 and frontal flanges 22 allowing upward or downward movement of positioning arm 35.

As stated, a primary objective of the present invention is to reduce the force which is necessary to reposition fluid containers 15. An understanding of the pulley assembly used to meet this objective can be best gained by reference to FIG. 3. As shown in FIG. 4 and FIG. 5, first pulley 41 is coupled to fluid hanger 14 and is disposed within cavity 43. A second pulley 60 is suitable journeled about a fixed axle 61 and is disposed within cavity 43. The diameter of second pulley 60 is smaller than the width of cavity 43 of extruded track 12 and is therefore freely rotatable about axle 61.

Figure 3:
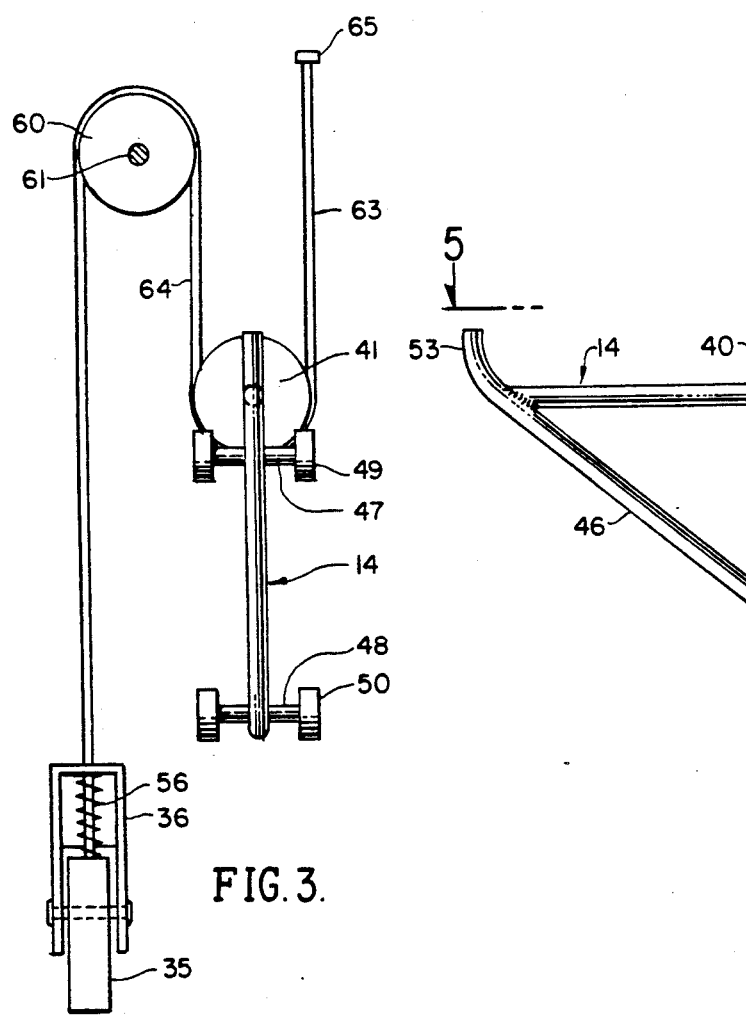
FIG. 3 is a schematic view of the pulley system linking the fluid hangers and respective positioning arms.

In the pulley configuration shown in FIG. 3 and FIG. 4, first pulley 41 is a moveable pulley and second pulley 60 is a fixed pulley. The weight imposed on fluid hanger 14 by fluid containers 15 will be suspended by two "falls" 63 and 64, each supporting one half of the total load. The sole function of second pulley 60 is to change the direction of fall 64, the extension thereof being coupled to positioning arm 35. The extension of fall 63 is secured to the upper terminus 65 of vertical standard 11. Using second pulley 60 as a fixed pulley and first pulley 41 as a moveable pulley, the load imposed on fluid hanger 14 may be raised by the application of a force on positioning arm 35 which is one-half as great as that of the load. This provides a mechanical advantage of 2:1.

It can therefore be seen the present invention provides an improved utility support apparatus to be used in medical applications. Using a pulley assembly, a mechanical advantage is gained. As a result thereof, heavy loads created by fluid containers can be raised through the application of a downwardly directed force which is a fraction of the actual load. When combined with enhanced stability, the present invention resolves those problems which are inherent in those devices disclosed by the prior art.

I claim:

1. An ambulatory supporting apparatus for movably supporting heavy loads comprising:
   (a) a central standard comprising a plurality of vertically disposed, parallel tracks;
   (b) a base including a hub coupled to said central standard, at least five supporting legs extending outwardly and upwardly from said hub and being uniformly spaced about said hub, and ambulatory means coupled to each of said supporting legs for movement over a horizontal surface;
   (c) hanger means for supporting the loads, said hanger means being slidably coupled within each of said parallel tracks;
   (d) a positioning arm slidably coupled within each of said parallel tracks; and
   (e) force transfer means coupled intermediate each of said load supporting hanger means and a respective positioning arm for moving said hanger means within said track in an inverse response to the movement of said positioning arm.

2. An ambulatory supporting apparatus as defined in claim 1 wherein said tracks each comprise a rear wall, a pair of side walls integral with and perpendicular to each end of said rear wall and first and second aligned frontal flanges parallel to said rear wall and depending inwardly from said side walls and first and second aligned interior flanges depending inwardly from said side walls between said frontal flanges and said rear wall, said first and second frontal flanges proscribing a longitudinal aperture therebetween in communication with a first cavity bounded by said rear wall, side walls and said first and second interior flanges and a second cavity bounded by said side walls, said first and second interior flanges and said first and second aligned frontal flanges.

3. An ambulatory supporting apparatus as defined in claim 2 wherein said hanger means comprises a horizontal supporting rod extending through the aperture proscribed by said first and second aligned frontal flanges and into said first cavity, and roller means coupled to said horizontal supporting rod for supporting said rod slidingly disposed within said second cavity bounded by said first and second frontal flanges and said first and second interior flanges.

4. An ambulatory supporting apparatus as defined in claim 3 wherein said force transfer means comprises:
   (a) a first pulley rotatably journeled about said horizontal supporting rod within the first cavity of said track bounded by said rear wall and said first and second interior flanges;
   (b) a second pulley rotatably coupled about an axle extending between the rear wall and first and second interior flanges and disposed within the first cavity bounded by the rear wall and said first and second interior flanges; and
   (c) positional means coupled to said first and second pulleys and to said positioner arm for transferring directional movement to said horizontal supporting rod in an inverse relationship to the direction of movement of said positioner arm.

5. An ambulatory supporting apparatus comprising:
   (a) a base consisting of a hub and at least five equally separated supporting legs extending outwardly and upwardly from said hub, the end of each of said supporting leg opposite said hub being coupled to a rotatable roller;
   (b) a plurality of extruded tracks placed adjacent one another and having first and second ends, the second ends of said extruded tracks being coupled to said hub and extending upwardly therefrom, each of said tracks comprising a rear wall, a pair of side walls integral with and perpendicular to said rear wall, first and second aligned frontal flanges parallel to said rear wall and depending inwardly from said side walls and defining a longitudinal aperture therebetween extending from the first end to the second end of said track in communication with a first cavity bounded by said rear wall, side walls and first and second interior flanges and a second cavity bounded by said first and second interior flanges and said first and second aligned frontal flanges, the longitudinal apertures of said adjacent tracks being separated by 90° of arc;
   (c) a load supporting hanger, and end thereof being in communication with the first and second cavities of each of said tracks, each said load supporting hanger including a horizontal supporting rod extending between said first and second frontal flanges of said respective track and into the first cavity and roller means coupled to said horizontal supporting rod for supporting said adjacent said supporting rod and being rollingly disposed within said second cavity;
   (d) a positioning arm slidably coupled within each of said extruded tracks and extending between said first and second frontal flanges and into said first cavity;
   (e) an engagement lever coupled to said positioning arm and adapted to resiliently exert frictional force against first and second frontal flanges; and
   (f) force transfer means coupled intermediate said load supporting hanger and a respective one of said positioning arms for moving said load supporting hanger within said extruded track and inverse response to the movement of said positioning arm.

6. An ambulatory supporting apparatus as defined in claim 5 wherein force transfer means comprises:
   (a) a first pulley rotatably journeled about said horizontal supporting rod within the first cavity of said extruded track;
   (b) a second pulley rotatably coupled about an axle extending between and being perpendicular to the rear wall and first and second frontal flanges of each of said extruded tracks and being rotatably disposed within the first cavity; and
   (c) positional means coupled to said first and second pulley and to said positioner arm for transferring directional movement to said horizontal supporting rod in an inverse relationship to the direction of movement of said positioner arm.

* * * * *

Adverse Decisions In Interference

Patent No. 5,188,323, Henry B. David, AMBULATORY SUPPORT APPARATUS, Interference No. 103,755, final judgment adverse to the patentee rendered October 24, 1997, as to claims 1-6.
*(Official Gazette June 2, 1998)*